US006319696B1

(12) United States Patent
Kishino et al.

(10) Patent No.: US 6,319,696 B1
(45) Date of Patent: *Nov. 20, 2001

(54) PROCESS FOR PRODUCING L-AMINO ACIDS

(75) Inventors: Hiroko Kishino; Masako Izui; Yukiko Ono; Hisao Ito; Osamu Kurahashi, all of Kawasaki (JP)

(73) Assignee: Ajinomoto Co., Inc., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,762
(22) PCT Filed: Aug. 27, 1996
(86) PCT No.: PCT/JP96/02399
§ 371 Date: Apr. 17, 1998
§ 102(e) Date: Apr. 17, 1998
(87) PCT Pub. No.: WO97/08333
PCT Pub. Date: Mar. 6, 1997

(30) Foreign Application Priority Data

Aug. 30, 1995 (JP) .................................................. 7-221561
Jul. 30, 1996 (JP) .................................................. 8-200860

(51) Int. Cl.[7] .............................. C12P 13/08; C12P 13/06
(52) U.S. Cl. ............................................ 435/115; 435/116
(58) Field of Search ...................................... 435/106, 108, 435/116, 193, 115; 536/23.2

(56) References Cited

U.S. PATENT DOCUMENTS

| 4,968,609 | | 11/1990 | Ito et al. ............................ 435/108 |
| 5,175,107 | * | 12/1992 | Debabv et al. ................. 435/252.33 |
| 5,236,831 | * | 8/1993 | Katsumata et al. ................. 435/106 |
| 5,906,925 | * | 5/1999 | Liao ....................................... 435/72 |
| 5,998,178 | * | 12/1999 | Hashiguchi et al. ................. 435/116 |

FOREIGN PATENT DOCUMENTS

| 2-000472 | 1/1990 | (JP) . |
| 7-203980 | 8/1995 | (JP) . |
| WO 96/08567 | 3/1996 | (WO) . |

OTHER PUBLICATIONS

Zubay, G. in Bichemistry, The Benjamin/Cummings Publishing Company, Inc., Menlo Park, California, Jul. 1986.*

* cited by examiner

Primary Examiner—Nashaat T. Nashed
(74) Attorney, Agent, or Firm—Oblon, Spivak, McClelland, Maier & Neustadt, P.C.

(57) ABSTRACT

A microorganism, which has an ability to produce L-amino acid, especially L-phenylalanine, L-tryptophane, L-tyrosine, L-threonine, or L-isoleucine, in which a phosphoenolpyruvate-producing ability is enhanced, is cultivated in a medium so that the L-amino acid is produced and accumulated in the medium to collect the L-amino acid.

6 Claims, 4 Drawing Sheets

H : HindIII
P : PstI
K : KpnI
B : BamHI
X : XbaI
Sm : SmaI
S : SalI
& : Impossible to re-cleave
P→ : Promoter

US 6,319,696 B1

PROCESS FOR PRODUCING L-AMINO ACIDS

TECHNICAL FIELD

The present invention relates to a method for producing L-amino acid. In particular, the present invention relates to a method for efficiently producing amino acid for which the demand rapidly increases, such as those used for a raw material for a sweetener aspartame (L-phenylalanine), feed additives (L-tryptophane, L-threonine), and raw materials for pharmaceuticals such as infusion solution (L-tryptophane, L-phenylalanine, L-tyrosine, L-threonine, and L-isoleucine).

BACKGROUND ART

There are a large number of methods for producing amino acid based on the use of the microorganism.

For example, methods for producing L-phenylalanine are known, including those based on the use of recombinants of *Escherichia coli* (*E. coli*) as disclosed in Japanese Patent Publication No. 2-4276, Japanese Laid-Open Patent Publication (PCT) No. 4-501813, Japanese Laid-Open Patent Publication No. 5-244956, and International Publication WO87/00202.

Methods for producing L-phenylalanine or L-tyrosine are also known, including those based on the use of a mutant strain belonging to the genus Corynebacterium as disclosed in Japanese Laid-Open Patent Publication No. 61-128897, and those based on the use of a recombinant of Corynebacterium strain as disclosed in Japanese Laid-Open Patent Publication Nos. 60-34197, 60-24192, 61-260892, and 61-124375.

Methods for producing L-tryptophane have been reported, including those based on the use of a recombinant of *Escherichia coli* as disclosed in Japanese Laid-Open Patent Publication No. 57-71397 and U.S. Pat. No. 4,371,614, those based on the use of a mutant strain of *Bacillus subtilis* as disclosed in Japanese Patent Publication Nos. 53-39517 and 62-34399, those based on the use of a recombinant of *Bacillus subtilis* as disclosed in Japanese Laid-Open Patent Publication Nos. 61-104790 and 1-67179, those based on the use of a mutant strain belonging to the genus Brevibacterium as disclosed in Japanese Laid-Open Patent Publication No. 57-174096, and those based on the use of a recombinant belonging to the genus Brevibacterium as disclosed in Japanese Laid-Open Patent Publication No. 62-51980.

Methods for producing L-threonine have been reported, including those based on the use of a mutant strain belonging to the genus Escherichia as disclosed in Japanese Laid-Open Patent Publication No. 5-304969, those based on the use of a recombinant of *Escherichia coli* as disclosed in Japanese Patent Publication No. 1-29559, Japanese Laid-Open Patent Publication Nos. 2-109985 and 56-15696, and Japanese Laid-Open Patent Publication (PCT) No. 3-501682. Further, there have been reported those based on the use of a mutant strain of a bacterium belonging to the genus Corynebacterium as disclosed in Japanese Laid-Open Patent Publication No. 62-239996, and those based on the use of a recombinant bacterium belonging to the genus Corynebacterium as disclosed in Japanese Laid-Open Patent Publication No. 61-195695.

Methods for producing L-isoleucine have been reported, including those based on the use of *Escherichia coli* as disclosed in Japanese Laid-Open Patent Publication No. 5-130882, and those based on the use of a recombinant of *Escherichia coli* as disclosed in Japanese Laid-Open Patent Publication No. 2-458. Further, there have been reported those based on the use of a mutant strain of a bacterium belonging to the genus Corynebacterium as disclosed in Japanese Patent Publication No. 3-62395, and those based on the use of a recombinant belonging to the genus Corynebacterium as disclosed in Japanese Patent Publication No. 5-47196.

The microorganisms, which have been used in the methods for producing amino acid as described above, have been bred principally on the basis of the enhancement of enzymes for catalyzing reactions in common pathways for various amino acids and in inherent pathways subsequent thereto for individual amino acids, or on the basis of the avoidance of control effected by final products or the like (feedback inhibition and suppression). Specifically, those which have been employed for the breeding include, for example, addition of auxotrophy to the microorganism, addition of drug resistance, and amplification of enzyme genes concerning the biosynthesis system and introduction of mutation aimed at desensitization of control based on the recombinant DNA technique.

The enzyme, which is in charge of the first reaction in the common pathway of aromatic amino acid biosynthesis, is 3-deoxy-D-arabino-hepturonate-7-phosphate (DAHP) synthase (DS). DS of *Escherichia coli* includes three types of isozymes which are encoded by genes called aroF, aroG, and aroH respectively and which undergo feedback inhibition by L-tyrosine, L-phenylalanine, and L-tryptophane respectively. Concerning these genes, a technique for improving the productivity of aromatic amino acid is known, which is based on the introduction, into *Escherichia coli*, of a combination of a gene coding for a desensitized type enzyme (enzyme substantially not subjected to feedback inhibition) originating from aroF or aroG involving high enzyme activity and a tryptophane operon containing a gene coding for a desensitized type anthranilate synthase (AS) of the inherent system of L-tryptophane biosynthesis.

Phosphoenclpyruvic acid (hereinafter referred to as "PEP" and D-erythrose 4-phosphate (E4 P) are used as substrates in the synthetic reaction for DAHP. PEP also serves as precursors for biosynthesis of L-aspartic acid, L-threonine, L-isoleucine and the like. The substrates as described above are supplied from a carbon source such as glucose via the glycolytic pathway and the pentoses phosphate pathway. However, no case has been hitherto known in the breeding of amino acid-producing strains, in which the ability to supply such substrates is enhanced to improve the productivity of amino acid.

Phosphoenolpyruvate synthase (hereinafter abbreviated as "PPS" is an enzyme which is broadly found in the microorganism. This enzyme plays an important role to supply PEP from pyruvic acid in glyconeogenesis. *Escherichia coli*, which is a bacterium belonging to the genus Escherichia, has been used to perform cloning of a gene (pps) coding for PPS, determination of the nucleotide sequence of the gene, and functional analysis for the enzyme. Besides, it has been reported that DAHP is produced at a value approximate to the theoretical yield by means of simultaneous amplification of the pps gene and the transketorase gene in a dehydroquinate synthase-deficient strain (Patnaik, R. et al., *Appl. Environ. Mircobiol.*, Vol. 60, No. 11, 3903–3908 (1994)). However, there has been known no case in which amplification of the pps gene enhances the productivity of aromatic amino acids and other amino acids.

DISCLOSURE OF THE INVENTION

An object of the present invention is to provide a method for producing various amino acids represented by aromatic amino acids inexpensively and at a high yield.

The present inventors have found out that the productivity of L-amino acids can be improved by enhancing the phosphoenolpyruvate-producing ability in cells of a microorganism which has the L-amino acid-producing ability. Thus, the present invention has been completed.

That is, the present invention lies in a method for producing L-amino acid comprising the steps of cultivating, in a medium, a microorganism having an L-amino acid-producing ability, producing and accumulating the L-amino acid in the medium, and collecting the L-amino acid, wherein:

a phosphoenolpyruvate-producing ability of the microorganism is enhanced.

The L-amino acid, which is preferably produced by the production method described above, includes L-tryptophane, L-phenylalanine, L-tyrosine, L-threonine, and L-isoleucine.

The microorganism having the L-amino acid-producing ability is exemplified by bacteria belonging to the genes Escherichia and coryneform bacteria. The coryneform bacteria referred to herein include bacteria which have been hitherto classified into those belonging to the genus Brevibacterium but which are unified into bacteria belonging to the genus Corynebacterium at present (*Int. J. Syst. Bacteriol.*, 41, 255 (1991)). Further, the coryneform bacteria referred to herein include bacteria belonging to the genus Brevibacterium which are extremely closely related to the genus Corynebacterium.

A means for enhancing the phosphoenolpyruvate-producing ability of the microorganism is, for example, to enhance an activity of PPS in microbial cells. Means for enhancing the activity of PPS in the microbial cells include, for example, a method to increase an amount of expression of a pps gene in the microbial cells, as well as a method to introduce, into the cells, a gene cording for PPS having a high specific activity.

Specifically, means for increasing the amount of expression of the pps gene in the microbial cells include, for example, a method to increase a copy number of the pps gene in the microbial cells, as well as a method to enhance a transcriptive activity of a promoter for the pps gene.

The present invention will be explained in detail below.

The microorganism preferably used in the present invention is not specifically limited, and it includes, for example, microorganisms belonging to the genera Escherichia, Brevibacterium, Corynebacterium, Bacillus, Serratia, and Pseudomonas, provided that a DNA fragment containing a replication origin of a plasmid is obtained for the microorganism, the pps gene functions in the microorganism, the copy number of the pps gene can be increased in the microorganism, and the microorganism has the L-amino acid-producing ability (for example, in the case of L-phenylalanine, those acquired the L-phenylalanine-producing ability by conferring, for example, resistance to L-phenylalanine analog). Among them, those preferably used are bacteria belonging to the genus Escherichia and the coryneform bacteria.

Specifically, those preferably used for L-tryptophane include, for example, *Escherichia coli* AGX17(pGX44) [NRRL B-12263] and AGX6(pGX50)aroP [NRRL B-12264] (see U.S. Pat. No. 4,371,614 for any of them), and *Brevibacterium flavum* AJ11667 (see Japanese Laid-Open Patent Publication No. 57-174096);

those preferably used for L-phenylalanine include, for example, *Escherichia coli* AJ12604 (FERM BP-3579) (see European Patent Publication No. 488,424), and *Brevibacterium lactofermentum* AJ12637 (FERM BP-4160) (see French Patent Publication No. 2,686, 898);

those preferably used for L-tyrosine include, for example, *Corynebacterium glutamicum* AJ11655 (FERM P-5836) (see Japanese Patent Publication No. 2-6517), and *Brevibacterium lactofermentum* AJ12081 (FERM P-7249) (see Japanese Laid-Open Patent Publication No. 60-70093);

those preferably used for L-threonine include, for example, *Escherichia coli* VKPM B-3996 (RIA 1867) (see U.S. Pat. No. 5,175,107), and *Corynebacterium acetoacidophilum* AJ12318 (FERM BP-1172) (see U.S. Pat. No. 5,188,949); and those preferably used for L-isoleucine include, for example, *Escherichia coli* KX141 (VKPM B-4781) (see European Patent Publication No. 519,113), and *Brevibacterium flavum* AJ12149 (FERM BP-759) (see U.S. Pat. No. 4,656,135).

The means for enhancing the PEP-producing ability of the microorganism as described above includes the enhancement of the PPS activity in the microbial cells.

The means for enhancing the PPS activity includes the increase of the amount of expression of the pps gene in the microbial cells. One of the means for enhancing the PPS activity is to modify the pps gene to create PPS having enhanced activity.

The means for increasing the amount of expression of the pps gene in the microbial cells includes the increase of the copy number of the pps gene in the microbial cells. In order to increase the copy number of the pps gene, it is necessary to obtain a DNA fragment containing the same gene. The pps gene has been cloned in *Escherichia coli* as a bacterium belonging to the genus Escherichia, and its nucleotide sequence has been determined (*Mol. Gen. Genet.*, 231, 332 (1992)). Accordingly, the preparation of the DNA fragment containing the same gene is achieved by using a method disclosed in the document described above. A desired DNA fragment can be obtained by using a hybridization method based on the use of a synthetic DNA probe prepared with reference to the nucleotide sequence described above, or by using a PCR (Polymerase Chain Reaction) method based on the use of synthetic DNA primers prepared with reference to the same nucleotide sequence. The copy number of the pps gene can be increased by ligating the DNA fragment containing the pps gene with a vector DNA autonomously replicable in a target microorganism, and introducing an obtained recombinant DNA fragment into the same microorganism.

The DNA primers, which are used to clone the pps gene from a bacterium belonging to the genus Escherichia by using the PCR method, can be appropriately prepared on the basis of, for example, a sequence known for *Escherichia coli* (*Mol. Gen. Genet.*, 231, 332 (1992)).

Specifically, two primers of

5'-CCCGTCGACGGATCCAGTTTCATCTCTTG-3' (SEQ ID NO: 1), and

5'-CCCGTCGACGATCATGCGCTTATGTCGTG-3' (SEQ ID NO: 2)

are suitable, which make it possible to amplify a region of about 3.3 kb containing the pps gene. These primers make it possible to amplify the pps gene in a form of having SalI cleavage ends at both terminals. When the restriction enzyme cleavage ends are introduced into the terminals of the PCR product, then the amplified DNA fragment is conveniently cloned by using the corresponding restriction enzyme, and the DNA fragment is conveniently transferred to another vector DNA. The primer DNA's can be synthesized, for example, by using a DNA synthesizer model 380B produced by Applied Biosystems in accordance with the phosphoamidite method (see *Tetrahedron Letters*, 22, 1859 (1981)). The PCR reaction can be performed, for example, by using DNA Thermal Cycler PJ2000 Type produced by Takara Shuzo and using Taq DNA polymerase in accordance with the method designated by the supplier.

The DNA fragment containing the pps gene can be also obtained from microorganisms other than the bacteria belonging to the genus Escherichia. The method for obtaining the DNA fragment includes a hybridization method based on the use of a synthetic DNA probe prepared with reference to the nucleotide sequence disclosed in the document described above (*Mol. Gen. Genet.*, 231, 332 (1992)), or by using a PCR method based on the use of synthetic DNA primers prepared with reference to the same nucleotide sequence. The DNA probe used for the hybridization method can be also appropriately prepared on the basis of the known sequence in the same manner as the DNA primers used for the PCR method. It is assumed that the nucleotide sequence of the gene differs depending on respective microorganisms. Therefore, it is desirable to prepare synthetic DNA which pairs with a portion conserved for PPS of each of the microorganisms.

When the pps gene amplified in accordance with the PCR method is introduced into a bacterium belonging to the genus Escherichia, then it is ligated with vector DNA autonomously replicable in cells of the bacterium belonging to the genus Escherichia, and obtained recombinant DNA is introduced into cells of the bacterium belonging to the genus Escherichia.

When the obtained DNA fragment containing the pps gene is introduced into a microorganism other than the bacteria belonging to the genus Escherichia, the DNA fragment is ligated with vector DNA autonomously replicable in cells of the microorganism for introducing the DNA fragment thereinto, and obtained recombinant DNA is introduced into the cells.

Plasmid vector DNA is preferably used as the vector DNA to be used in the present invention. When the microorganism into which the gene is introduced is *Escherichia coli*, those usable as the vector DNA include, for example, pTWV228, pUC19, pUC18, pBR322, pHSG299, pHSG399, and RSF1010. Besides, vectors composed of phage DNA may be utilized. In order to achieve efficient expression of PPS, it is also preferable to use a promoter which functions in the microorganism, such as lac, trp, and $P_L$. In order to increase the copy number of the pps gene, it is also preferable to incorporate DNA containing the pps gene into the chromosome in accordance with the method based on the use of transposon (Berg, D. E. and Berg, C. M., *Bio/Technol.*, 1, 417 (1983)), Mu phage (Japanese Laid-Open Patent Publication No. 2-109985), or homologous recombination (*Experiments in Molecular Genetics*, Cold Spring Harbor Lab. (1972)).

As for the vector DNA to be used in the present invention, when the microorganism into which the gene is introduced is the coryneform bacteria, those usable as the vector DNA include, for example, plasmid vectors autonomously replicable in the coryneform bacteria, such as pAM330 (see Japanese Patent Publication No. 1-11280) and pHM1519 (see Japanese Laid-Open Patent Publication No. 58-77895).

*Escherichia coli* may be transformed with the recombinant vector obtained by inserting the DNA sequence of the present invention into the vector as described above, by using, for example, a method which is usually used for transformation of *Escherichia coli*, such as a method to enhance the permeability of DNA by treating cells with calcium chloride (Mandel, M. and Higa, A., *J. Mol. Biol.*, 53, 159 (1977)).

The method for transforming bacteria belonging to the genus Bacillus includes a method in which incorporation is performed during a specified growth period in which cells are able to incorporate DNA (report on *Bacillus subtilis* submitted by Duncan, C. H. et al). Further, DNA can be incorporated into bacterial cells by forming protoplast or spheroplast as DNA recipient which easily incorporates plasmid DNA. These methods are known for *Bacillus subtilis*, Actinomyces, and yeasts (Chang, S. et al., *Molec. Gen. Genet.*, 168, 111 (1979); Bibb et al., *Nature*, 274, 398 (1978); Hinnen, A. et al., *Proc. Natl. Acad. Sci. USA*, 75, 1929 (1978)).

The electroporation method, in which pores are instantaneously formed through cell walls by means of high voltage electric pulse so that DNA is incorporated (Hanahan, D. et al., *Plasmid Transformation of Escherichia coli and other bacteria, Meth. Enzymol.*, 204, 63 (1991)), is also effective for a broad range of microbial cells. Besides, a transformation method based on the electroporation method for the coryneform bacteria is disclosed in Japanese Laid-Open Patent Publication No. 2-207791.

In order to select a vector into which the pps gene is actually introduced, from candidate vectors which have the possibility of introduction of the pps gene, for example, a complementation test may be performed by using a PPS-deficient strain. The PPS-deficient strain cannot grow on a minimum medium containing pyruvic acid as a sole carbon source. Therefore, a transformant, which is capable of growing on this medium, may be selected. The PPS-deficient strain of *Escherichia coli* includes AT2572-1 strain (see *J. Bacteriol.*, 96, 2185 (1968)). AT2572-1 strain is obtainable from *E. coli* Genetic Stock Center (Yale University, Dept. Biology, Osborn Memorial Labs., 06511-7444 New Haven, Conn., U.S.A., P.O. Box 6666, Strain No: CGSC5242).

In order to select a strain in which the PPS activity is actually enhanced, from candidate strains which have the possibility of increase in the PPS activity, for example, a method is available, in which the increase in PPS enzyme activity is confirmed by using a known method (Cooper, R. A. and H. L. Kornberg, *Meth. Enzymol.*, 13, 309 (1969)).

The microorganism preferably used for the present invention includes those obtained by enhancing the PEP-producing ability of a microorganism which originally has the L-amino acid-producing ability, and those obtained by adding the L-amino acid-producing ability after enhancing the PEP-producing ability. Further, even in the case of a microorganism which originally has the L-amino acid-producing ability, the L-amino acid-producing ability is still more improved in some cases by enhancing an enzyme gene which is in charge of an inherent pathway in biosynthesis of the corresponding amino acid, or by introducing an operon or a gene which codes for a desensitized type (inhibition-desensitized type) enzyme of an enzyme which would be otherwise subjected to feedback inhibition.

The gene or the operon as described above is exemplified by:

those for L-phenylalanine and L-tyrosine, including, for example, desensitized type chorismate mutase-prephenate dehydratase (CM-PDT) gene (see Japanese Laid-Open Patent Publication Nos. 5-236947 and 62-130693) and desensitized type DS (3-deoxy-D-arabino-hepturonate-7-phosphate synthase) gene (see Japanese Laid-Open Patent Publication Nos. 5-236947 and 61-124375);

those for L-tryptophane, including, for example, tryptophane operon containing a gene coding for desensitized type anthranilate synthase (Japanese Laid-Open Patent Publication Nos. 57-71397 and 62-244381, and U.S. Pat. No. 4,371,614);

those for L-threonine, including, for example, threonine operon having a gene coding for aspartokinase for which feedback inhibition by L-threonine is desensitized (Japanese Patent Publication No. 1-29559), a gene coding for homoserine dehydrogenase (Japanese Laid-Open Patent Publication No. 60-012995), and a gene coding for homoserine kinase and homoserine dehydrogenase (Japanese Laid-Open Patent Publication No.

those for L-isoleucine, including, for example, threonine operon described above and a gene coding for threonine deaminase for which feedback inhibition by L-isoleucine is desensitized (Japanese Laid-Open Patent Publication No. 2-458).

As for the aromatic amino acids (L-phenylalanine, L-tryptophane, and L-tyrosine), it is expected that the productivity can be still more improved by enhancing the producing ability for transketorase (TK) in cells in addition to PPS. The means for enhancing the TK-producing ability of the microorganism includes the enhancement of the TK activity in microbial cells. The means for enhancing the TK activity includes the increase of the expression amount of the transketorase gene (tkt) in microbial cells. One of the means to enhance the TK activity includes modification of the tkt gene to create TK having enhanced activity.

The means for increasing the amount of expression of the tkt gene in the microbial cells includes the increase of the copy number of the tkt gene in the microbial cells. In order to increase the copy number of the tkt gene, it is necessary to obtain a DNA fragment containing the same gene. The tkt gene has been cloned in *Escherichia coli* as a bacterium belonging to the genus Escherichia, and its nucleotide sequence has been determined (*Biochim. Biophys. Acta*, 1216, 307 (1993)). Accordingly, the preparation of the DNA fragment containing the same gene is achieved by using a method disclosed in the document described above. A desired DNA fragment can be obtained by using a hybridization method based on the use of a synthetic DNA probe prepared with reference to the nucleotide sequence described above, or by using a PCR (Polymerase Chain Reaction) method based on the use of synthetic DNA primers prepared with reference to the same nucleotide sequence. The copy number of the transketorase gene can be increased by ligating the DNA fragment containing the tkt gene with a vector DNA autonomously replicable in a target microorganism, and introducing an obtained recombinant DNA fragment into the same microorganism.

The DNA primers, which are used to clone the transketorase gene from a bacterium belonging to the genus Escherichia by using the PCR method, can be appropriately prepared on the basis of, for example, a sequence known for *Escherichia coli* (*Biochim. Biophys. Acta*, 1216, 307 (1993)). Specifically, two primers of 5'-AGAGGATCCAGAGATTTCTGAAGC-3' (SEQ ID NO: 3), and

5'-TCTGGATCCGCAAACGGACATTATCA-3' (SEQ ID NO: 4)

are suitable, which make it possible to amplify a region of about 2.2 kb containing the tkt gene. These primers make it possible to amplify the tkt gene in a form of having BamHI cleavage ends at both terminals. When the restriction enzyme cleavage ends are introduced into the terminals of the PCR product, then the amplified DNA fragment is conveniently cloned by using the corresponding restriction enzyme, and the DNA fragment is conveniently transferred to another vector DNA. The primer DNA's can be synthesized, for example, by using a DNA synthesizer model 380B produced by Applied Biosystems in accordance with the phosphoamidite method (see *Tetrahedron Letters*, 22, 1859 (1981)). The PCR reaction can be performed, for example, by using DNA Thermal Cycler PJ2000 Type produced by Takara Shuzo and using Taq DNA polymerase in accordance with the method designated by the supplier.

The DNA fragment containing the tkt gene can be also obtained from microorganisms other than the bacteria belonging to the genus Escherichia. The method for obtaining the DNA fragment includes a hybridization method based on the use of a synthetic DNA probe prepared with reference to the nucleotide sequence disclosed in the document described above (*Biochim. Biophys. Acta*, 1216, 307 (1993)), or by using a PCR method based on the use of synthetic DNA primers prepared with reference to the same nucleotide sequence. The probe used for the hybridization can be also appropriately prepared on the basis of the known sequence in the same manner as the DNA primers used for the PCR method. It is assumed that the nucleotide sequence of the gene differs depending on respective microorganisms. Therefore, it is desirable to prepare synthetic DNA which pairs with a portion conserved for TK of each of the microorganisms.

When the respective genes as described above are introduced in-to the microorganism, each of the genes may exist on the chromosome of the host, or it may be exist on an identical plasmid, in the same manner as in the pps gene. Alternatively, the respective genes may exist on different plasmids.

The objective amino acid can be produced by cultivating the microorganism transformed with the recombinant DNA containing the pps gene obtained in accordance with the method described above, producing and accumulating the objective amino acid in a culture fluid, and collecting the objective amino acid.

The medium used for the cultivation is an ordinary medium containing a carbon source, a nitrogen source, inorganic ions, and optionally other organic components.

Those usable as the carbon source include, for example, sugars such as glucose, lactose, galactose, fructose, sucrose, and starch hydrolyzate; alcohols such as glycerol and sorbitol; and organic acids such as fumaric acid, citric acid, and succinic acid.

Those usable as the nitrogen source include, for example, inorganic ammonium salts such as ammonium sulfate, ammonium chloride, and ammonium phosphate; organic nitrogen such as soybean hydrolyzate; ammonia gas; and aqueous ammonia.

It is desirable to use, as the organic trace nutrient source, required substances such as vitamin B1 and vitamin B6, if necessary, as well as yeast extract or the like contained in an appropriate amount.

Besides, for example, small amounts of potassium phosphate, magnesium sulfate, iron ion, and manganese ion are added, if necessary.

The cultivation may be performed under a condition adapted to the microorganism to be used. Specifically, the cultivation is preferably carried out under an aerobic condition for 16 to 72 hours. The cultivation temperature is controlled to be 30° C. to 45° C., and pH is controlled to be 5 to 7 during the cultivation. For the purpose of pH adjustment, it is possible to use, for example, inorganic or organic acidic or alkaline substances as well as ammonia gas.

The L-amino acid can be collected from the fermentation fluid by combining known methods such as the ordinary ion exchange resin method, the precipitation method, and other methods.

BEST MODE FOR CARRYING OUT THE INVENTION

Figure 1:
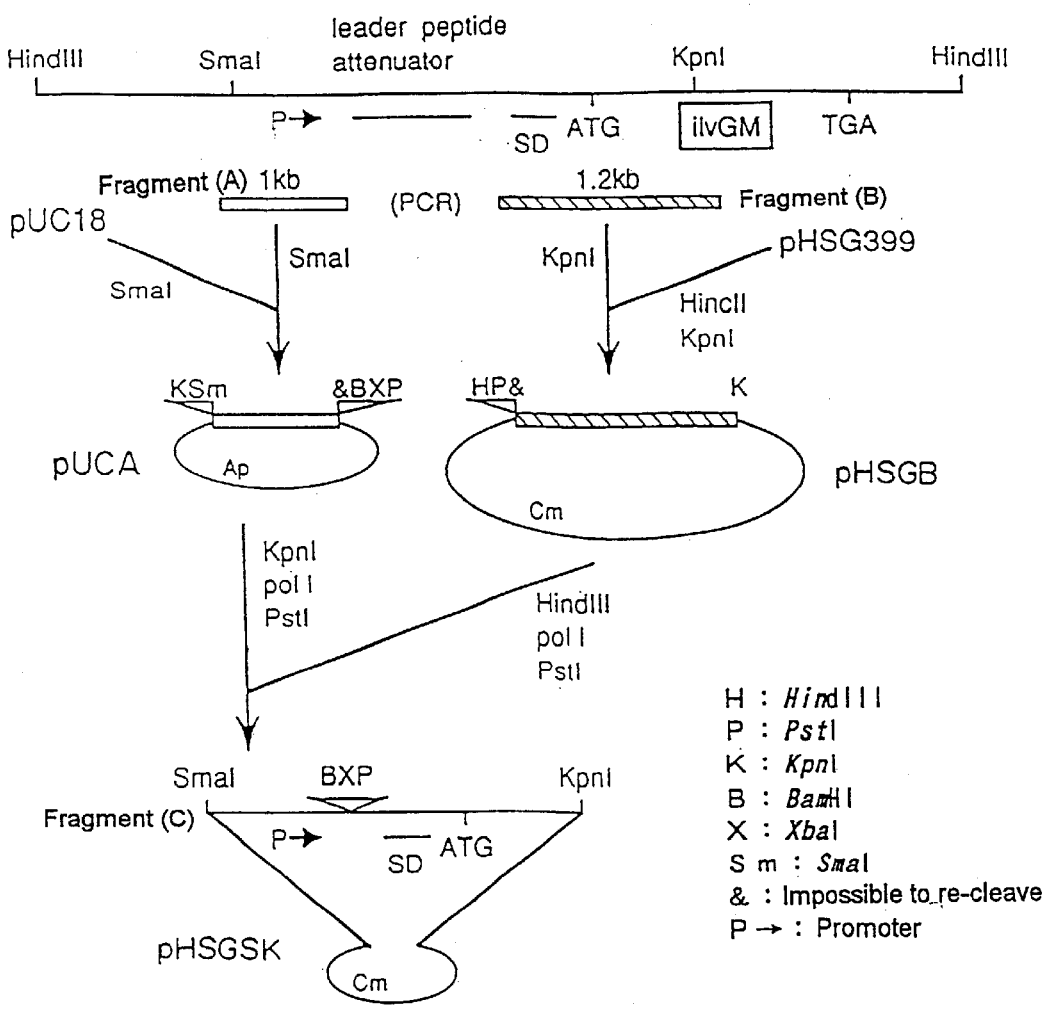
FIG. 1 shows a procedure for constructing a plasmid PHSGSK.

The present invention will be explained in further detail below with reference to Examples.

EXAMPLE 1

Preparation of pps Gene of *Escherichia coli*

Chromosomal DNA was extracted from W3110 strain originating from *Escherichia coli* K-12 in accordance with the method of Saito and Miura (*Biochem. Biophys. Acta*, 72, 619 (1963)). On the other hand, oligonucleotide primers to be used for amplifying the pps gene from the chromosomal DNA in accordance with the PCR method were synthesized on the basis of a known nucleotide sequence of the pps gene (*Mol. Gen. Genet.*, 231, 332 (1992)).

(1) 5'-CCCGTCGACGGATCCAGTTTCATCTCTTG-3' (SEQ ID NO: 1)

(2) 5'-CCCGTCGACGATCATGCGCTTATGTCGTG-3' (SEQ ID NO: 2)

The primers mentioned above contain sequences homologous to or complementary to sequences located on upstream and downstream sides of the pps gene respectively, and they contain SalI recognition sequences for facilitating cloning of the PCR product.

The PCR reaction was carried out by using the chromosomal DNA and the primers described above in accordance with the method of Erlich (*PCR Technology*, Stockton press (1989)). The reaction condition resided in a reaction cycle comprising thermal denaturation at 93° C. for 1 minute, annealing at 55° C. for 1.5 minute, and polymerase reaction at 72° C. for 3 minutes, the reaction cycle being repeated 30 times.

A DNA fragment of 3.3 kbp obtained by the PCR reaction was digested with a restriction enzyme SalI, followed by ligation to a SalI site of a plasmid vector pTWV228 (ampicillin resistance (Ap'), produced by Takara Shuzo) by using DNA ligase. A PPS-deficient strain AT2572-1 of *Escherichia coli* (see *J. Bacteriol.*, 96, 2185 (1968), obtained from *E. coli* Genetic Stock Center (the above-mentioned address)) was transformed with the ligation reaction mixture. Transformants were spread on a plate containing ampicillin to select grown ampicillin-resistant strains from which a strain growable on a minimum medium by using pyruvic acid as a carbon source was selected. Plasmid DNA was extracted from the strain, and the obtained plasmid was designated as pTWV-pps.

A restriction enzyme cleavage map was analyzed for an insert DNA fragment of pTWV-pps obtained as described above, and the PPS activity of the obtained transformant was measured. According to results of the analysis and the measurement, it was confirmed that the DNA fragment contained the pps gene.

EXAMPLE 2

Production of L-Phenylalanine

<1>Creation of L-Phenylalanine-Producing Bacterium

A DNA fragment containing a desensitized type chorismate mutase-prephenate dehydratase (CM-PDT) gene of the inherent system for L-phenylalanine biosynthesis was inserted into BamHI, HindIII cleavage sites of a plasmid vector pACYC184 (Cm') to obtain a plasmid pACMAB (chloramphenicol resistance (Cm'), see Japanese Laid-Open Patent Publication No. 5-236947) which was digested with SalI. An obtained fragment was ligated with a pps gene fragment excised from pTWV-pps with SalI, by using DNA ligase to obtain pACMAB-pps (8.9 kb).

On the other hand, a DNA fragment containing desensitized type DS (3-deoxy-D-arabino-hepturonate-7-phosphate synthase) gene (aroG4) was inserted into EcoRI, HindIII cleavage sites of a plasmid vector pBR322 to obtain a plasmid pBR-aroG4 (Ap', see Japanese Laid-Open Patent Publication No. 5-236947) with which *Escherichia coli* W3110 (tyrA) strain was transformed. pACMAB-pps was introduced into an obtained transformant strain to select a transformant exhibiting Ap' and Cm' to obtain W3110 (tyrA)/pACMAB-pps,pBR-aroG4.

The tyrA-deficient strain W3110 (tyrA) (designated as AJ12604) of *Escherichia coli* transformed with pBRaroG4 and pACMAB has been deposited on Jan. 28, 1991 in National Institute of Bioscience and Human Technology of Agency of Industrial Science and Technology of Ministry of International Trade and Industry (zip code: 305, 1-3 Higashi 1-Chome, Tsukuba-shi, Ibaraki-ken, Japan) under an accession number of FERM P-11975, transferred on Sep. 26, 1991 to international deposition based on the Budapest Treaty, and deposited under an accession number of FERM BP-3579. pBR-aroG4 and pACMAB are obtainable from this strain in accordance with an ordinary method.

<2>Evaluation of L-Phenylalanine Productivity

*Escherichia coli* W3110(tyrA)/pACMAB-pps,pBR-aroG4 strain obtained as described above was cultivated at 37° C. for 40 hours by using an L-phenylalanine-producing medium (containing 20 g of glucose, 29.4 g of disodium hydrogen-phosphate, 6 g of potassium dihydrogenphosphate, 1 g of sodium chloride, 2 g of ammonium chloride, 10 cl of sodium citrate, 0.4 g of sodium glutamate, 3 g of magnesium sulfate heptahydrate, 0.23 g of calcium chloride, 2 mg of thiamine hydrochloride, and 100 mg of L-tyrosine in 1 L of water, pH=7.0). W3110(tyrA)/plACMAB,pBR-aroG4 strain was cultivated as a control in the same manner as described above. L-Phenylalanine contained in the medium was quantitatively determined by means of high performance liquid chromatography. Results are shown in Table 1.

TABLE 1

| Bacterial strain | Amount of produced L-phenylalanine (g/L) |
| --- | --- |
| W3110 (tyrA)/pACMAB,pBR-aroG4 | 3.8 |
| W3110 (tyrA)/PACMAB-pps,pBR-aroG4 | 4.1 |

EXAMPLE 3

Production of L-Tryptophane

<1>Creation of L-Tryptophane-Producing Bacterium

A DNA fragment containing the desensitized type DS gene (aroG4) and a kanamycin-resistant gene was inserted into a plasmid pACYC177E obtained by modifying an XhoI site of a plasmid pACYC177 into an EcoRI site, to obtain a plasmid pACKG4 (resistant to ampicillin and kanamycin ($Ap^r$, $Km^r$), 6.4 kb, see Japanese Laid-Open Patent Publication No. 5-236947) which was partially digested with HindIII, and blunt-ended by using DNA polymerase Klenow fragment. On the other hand, the SalI fragment of 3.3 kbp containing the pps gene obtained in Example 1 was blunt-ended in the same manner as described above, and it was ligated with the pACKG4 fragment described above. The PPS-deficient strain of Escherichia coli was transformed with the ligation reaction solution to select a transformant exhibiting $Ap^r$, $Km^r$, and $pps^+$. A recombinant plasmid was extracted from the transformant, and it was designated as pACKG4-pps (9.4 kb).

Plasmid pGX44 was deleted from a bacterial strain, i.e., Escherichia coli AGX17(pGX44) strain having characters of L-phenylalanine and L-tyrosine auxotrophy (the host AGX 17 strain itself is L-phenylalanine, L-tyrosine, and L-tryptophane auxotrophy) to obtain AGX 17. On the other hand, pGX 50 was extracted from AGX6(pGX50) (arop) strain of Escherichia coli K-12 harboring a plasmid pGX50 ($Ap^r$) carrying tryptophane operon (described in U.S. Pat. No. 4,371,614, and deposited since Jan. 31, 1981 under an accession number of NRRL B-12264 in Agricultural Research Service Culture Collection (NRRL) (1815 North University Street, Peoria, Ill. 61604, United States of America)), and it was introduced into the AGX17 strain to select a transformant by using $Ap^r$ and $Trp^+$ as indexes. pACKG4-pps was further introduced into the transformant to select a transformant by using $Ap^r$ and $Km^r$ as indexes. The obtained transformant was designated as AGX17/pGX50,pACKG4-pps.

On the other hand, pGX50 and pACKG4 were introduced into AGX17 by using $Ap^r$, $Trp^+$, and $Km^r$ as indexes to obtain AGX17/pGX50,pACKG4.

<2>Evaluation of L-Tryptophane Productivity

AGX17/pGX50,pACKG4-pps was cultivated at 31° C. for 48 hours by using an L-tryptophane-producing medium (containing 40 g of glucose, 16 g of ammonium sulfate, 1 g of potassium primary phosphate, 1 g of magnesium sulfate heptahydrate, 0.01 g of ferrous sulfate heptahydrate, 0.01 g of manganese chloride tetrahydrate, 2 g of yeast extract, 40 g of calcium carbonate, 100 mg L-phenylalanine, and 100 mg of L-tyrosine in 1 L of water, pH=7.0). AGX17/pGX50, pACKG4 was cultivated as a control in the same manner as described above. L-Tryptophane contained in the medium was quantitatively determined by means of high performance liquid chromatography. Results are shown in Table 2.

TABLE 2

| Bacterial strain | Amount of produced L-tryptophane (g/L) |
| --- | --- |
| AGX17/pGX50,pACKG4 | 2.1 |
| AGX17/pGX50,pACKG4-pps | 2.5 |

EXAMPLE 4

Production of L-Threonine

<1>Creation of L-Threonine-Producing Bacterium pTWV-pps obtained in Example 1 was introduced into an L-threonine-producing bacterium, Escherichia coli VKPM B-3996 strain (described in United States Patent No. 5,175, 107, and deposited since November 19, 1987 under a registration number of RIA 1867 in All-Union Scientific Center of Antibiotics (VNIIA) (Nagatinskaya Street 3-a, 113105 Moscow, Russian Federation)). A transformant was selected on the basis of $Sm^r$ and $Ap^r$ to obtain B-3996/pTWV-pps. The VKPM B-3996 strain harbors a plasmid pVIC40 (streptomycin resistance ($Sm^r$)) containing threonine operon having a gene coding for aspartokinase in which feedback inhibition by L-threonine is desensitized.

<2>Evaluation of L-Threonine Productivity

B-3996 strain and B-3996/pTWV-pps were cultivated at 37° C. for 24 hours by using an L-threonine-producing medium (containing 40 g of glucose, 16 g of ammonium sulfate, 1 g of potassium primary phosphate, 1 g of magnesium sulfate heptahydrate, 0.01 g of ferrous sulfate heptahydrate, 0.01 g of manganese chloride tetrahydrate, 2 g of yeast extract, and 40 g of calcium carbonate in 1 L of water, pH=7.0). L-Threonine contained in the medium was quantitatively determined by means of high performance liquid chromatography. Results are shown in Table 3.

TABLE 3

| Bacterial strain | Amount of produced L-threonine (g/L) |
| --- | --- |
| B-3996 | 14.5 |
| B-3996/pTWV-pps | 15.5 |

EXAMPLE 5

Production of L-Isoleucine

<1>Creation of L-Isoleucine-Producing Bacterium (1) Construction of Plasmid Containing Threonine Operon and pps Gene A plasmid. pVIC40 containing threonine operon having a gene coding for aspartokinase desensitized with feedback inhibition by L-threonine (described in U.S. Pat. No. 5,175, 107) was digested with BamHI, and an obtained fragment was blunt-ended by using Klenow fragment. On the other hand, the SaiI fragment of 3.3 kbp containing the pps gene obtained in Example 1 was blunt-ended in the same manner as described above, and it was ligated with the pVIC40 fragment described above. The ligation reaction solution was used to transform Esaherichia coli PPS-deficient strain to select a transformant exhibiting Smw and ppsc. A recombinant plasmid was extracted from the transformant, and it was designated as pVIC40-pps (17.9 kb).

(2) Construction of Plasmid Containing IlvGMEDA Operon

Chromosomal DNA was extracted from Escherichia coli MI162 strain. The chromosomal DNA was digested with restriction enzyme HindIII. It has been revealed that a HindIII-HindIII DNA fragment containing the ilvGM gene has a length of 4.8 kb. Accordingly, a HindIII-HindIII DNA fragment having a length in the vicinity of 4.8 kb was ligated with a DNA fragment obtained by digesting a plasmid vector pBR322 (purchased from Takara Shuzo) with HindIII.

An obtained DNA ligation reaction mixture was introduced into Escherichia coli MI262 (CGSC5769) strain as an acetohydroxyacid synthase-deficient strain. A transformed strain, in which the character of deficiency of acetohydroxyacid synthase was complemented, was selected. A plasmid harbored by the strain was isolated. As a result of analysis of the structure of the plasmid, a DNA fragment of 4.8 kb containing the ilvGM gene and a part of the 5'-terminal side of the ilvE gene was inserted at the HindIII site of pBR322. The plasmid was designated as pBRGM7.

Synthetic oligonucleotides described in SEQ ID NO: 8 and SEQ ID NO: 9 in Sequence Listing were synthesized with reference to a nucleotide sequence of the ilvGM gene reported in Gene, 97, 21 (1991); Proc. Natl. Acad. Sci. U.S.A., 78, 922 (1981); and J. Bacteriol., 149, 294 (1982). A sequence containing promoter, attenuator, and an ilvGM gene-coding region of the nucleotide sequence of the ilvGM gene is depicted in SEQ ID NO: 5 together with an amino acid sequence of the coding region. The both oligonucleotides were used as primers to amplify DNA in accordance with the PCR method by using chromosomal DNA of MI162 strain as a template. The DNA fragment to be amplified is a DNA fragment having a sequence from 25th nucleotide to 952th nucleotide of the nucleotide sequence depicted in SEQ ID NO: 5 in Sequence Listing. This fragment was designated as "fragment (A)".

Synthetic oligonucleotides described in SEQ ID NO: 10 and SEQ ID NO: 11 in Sequence Listing were synthesized with reference to the nucleotide sequence reported in *Gene*, 97, 21 (1991); *Proc. Natl. Acad. Sci. U.S.A.*, 78, 922 (1981); and *J. Bacteriol.*, 149, 294 (1982), in the same manner as described above. The both oligonucleotides were used as primers to amplify DNA in accordance with the PCR method by using chromosomal DNA of MI162 strain as a template. The DNA fragment to be amplified is a DNA fragment having a sequence from 1161th nucleotide to 2421th nucleotide of the nucleotide sequence depicted in SEQ ID NO: 5 in Sequence Listing. This fragment was designated as "fragment (B)".

A large fragment obtained by digesting the fragment (A) with SmaI was ligated with a DNA fragment obtained by digesting a vector pUC18 (Takara Shuzo) with SmaI to prepare a plasmid PUCA. A large fragment obtained by digesting the fragment (B) with KpnI was ligated with a large fragment obtained by digesting pHSG399 (Takara Shuzo) with HincI and KpnI to prepare a plasmid PHSGB.

The plasmid pUCA was digested with KpnI, and the digested end was blunt-ended by using large fragment (Klenow fragment) of DNA polymerase I, followed by digestion with PstI to finally isolate a DNA fragment containing the fragment (A). The plasmid PHSGB was digested with HindIII, and the digested end was blunt-ended by using large fragment (Klenow fragment) of DNA polymerase I, followed by digestion with PstI to finally isolate a DNA fragment containing the fragment (B). The both DNA fragments were ligated with each other to prepare a plasmid PHSGSK.

The SmaI-KpnI fragment, which was carried on pHSGSK and originated from the fragments (A) and (B), was designated as "fragment (C)". The fragment (C) corresponds to a fragment obtained by digesting the HindIII-HindIII fragment of 4.8 kb containing the ilvGM gene with SmaI and KpnI, which contains promoter, SD sequence, and upstream region of the ilvG gene, but which lacks a sequence of about 0.2 kb ranging from leader sequence to attenuator region. The procedure for constructing pHSGSK as described above is summarized in FIG. 1.

Figure 2:
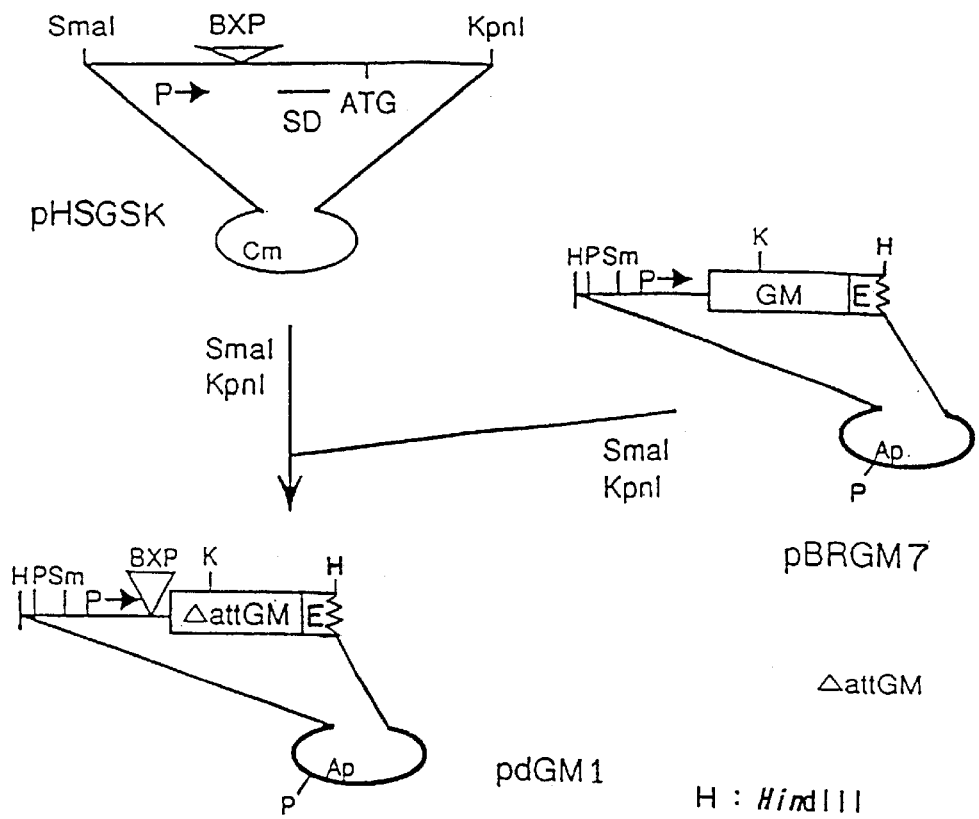
FIG. 2 shows a procedure for constructing a plasmid pdGM1.

The fragment (C) was obtained by digesting the plasmid PHSGSK with SmaI and KpnI. A large DNA fragment was obtained by digesting the plasmid pBRGM7 with SmaI and KpnI. The both fragments were ligated with each other. An obtained plasmid was designated as pdGM1. A HindIII-HindIII fragment of 4.6 kb containing the ilvGM gene, which is carried on pdGM1, lacks the region necessary for attenuation. The ilvGM gene, which lacks the region necessary for attenuation, is expressed as "ΔattGM" in this Example and the drawings. The procedure for constructing pdGM1 as described above is summarized in FIG. 2.

A plasmid pDRIA4, which is described in Japanese Laid-Open Patent Publication No. 2-458, is autonomously replicable in bacteria belonging to the genus Escherichia. The plasmid pDRIA4 is prepared by combining a shuttle vector pDR1120 autonomously replicable in bacteria belonging to the genus Brevibacterium with a BamHI-BamHI fragment containing ilvA gene coding for threonine deaminase originating from *E. coli* K-12 and a part of the 3'-terminal side of ilvD gene. The BamHI-BamHI fragment is described to be 2.3 kb in Japanese Laid-Open Patent Publication No. 2-458. However, at present, the BamHI-BamHI fragment has been revealed to be 2.75 kb. The plasmid pDRIA4 exists out of the chromosomal DNA of *Brevibacterium flavum* AJ12358 (FERM P-9764) or *Brevibacterium flavum* AJ12359 (FERM P-9765). The plasmid pDRIA4 can be prepared from these strains in accordance with an ordinary method.

A HindIII-BamHI fragment containing the ilvA gene coding for threonine deaminase substantially desensitized with inhibition by L-isoleucine was prepared from the BamHI-BamHI DNA fragment of 2.75 kb on the plasmid pDRIA4. The HindIII-BamHI fragment was ligated with a DNA fragment obtained by digesting a vector pMW119 (produced by Nippon Gene) with HindIII and BamHI. A plasmid thus prepared was designated as pMWA1.

Figure 3:
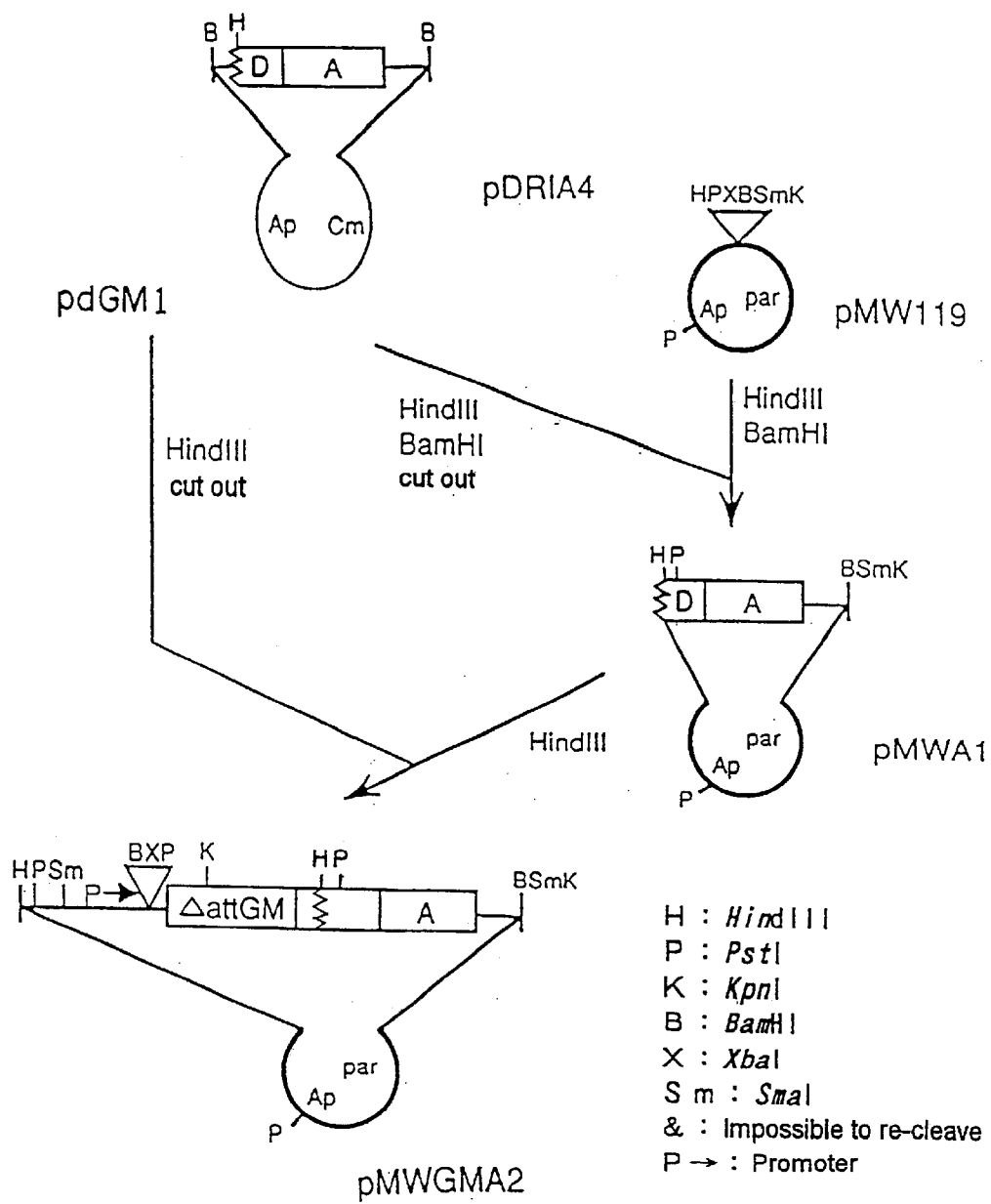
FIG. 3 shows a procedure for constructing a plasmid pMWGMA2.

A DNA fragment obtained by digesting the plasmid pMWA1 with HindIII was ligated with a DNA fragment containing the ilvGM gene obtained by digesting the plasmid pdGM1 with HindIII. A plasmid, in which the ilvGM gene had the same transcription direction as the transcription direction of the ilvA gene, was selected by analyzing the position of the restriction enzyme recognition site existing on the plasmid. The obtained plasmid was designated as pMWGMA2. pMWGMA2 has the ilvGM gene from which attenuator is removed, a part of the 5'-terminal side of the ilvE gene, and a part of the 3'-terminal side of the ilvD gene. The procedure for constructing p.MWGMA2 as described above is summarized in FIG. 3.

Figure 4:
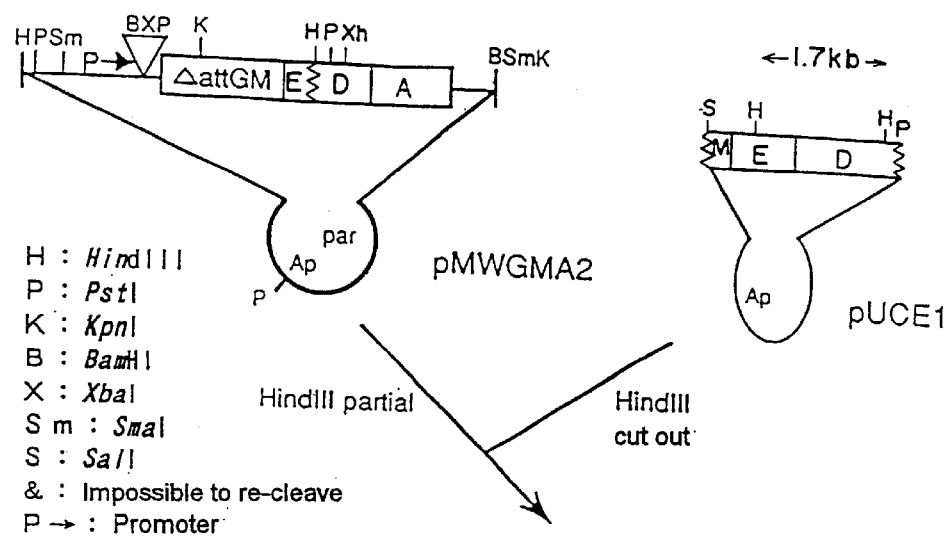
FIG. 4 shows a procedure for constructing a plasmid pMWD5.
Figure 4:
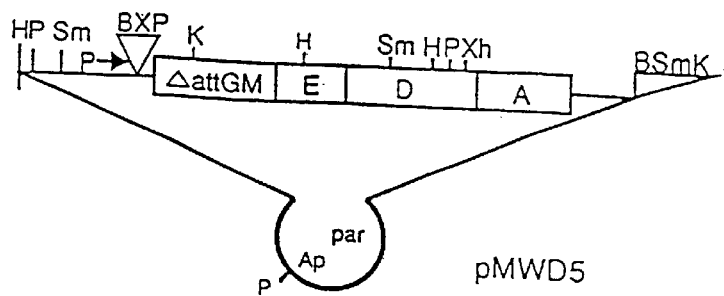

Chromosomal DNA of *Escherichia coli* MI162 strain was prepared, which was digested with SalI and PstI to prepare a DNA fragment mixture. On the other hand, a vector pUC19 (Takara Shuzo) was digested with SalI and PstI to prepare a DNA fragment. The DNA fragment mixture was ligated with the DNA fragment obtained by digesting pUC19 to obtain a DNA mixture. This DNA mixture was introduced into AB2070 strain as a transaminase B-deficient strain (*J. Bacteriol.*, 109, 703 (1972), allotted from *E. coli* Genetic Stock Center, CGSC2070) to select a transformed strain recovered with branched amino acid auxotrophy. When a plasmid was prepared from the obtained strain, the DNA fragment obtained by digesting the plasmid pUC19 with SalI and PstI was ligated with the SalI-PstI DNA fragment containing the ilvE gene. This plasmid was designated as pUCE1. pUCE1 includes a part of the 3'-terminal side of the ilvM gene, the ilvE gene, and a part of the 5'-terminal side of the ilvD gene.

pMWGMA2 was partially digested with HindIII to prepare a DNA fragment mixture. On the other hand, pUCE1 was digested with HindIII to prepare a HindIII-HindIII DNA fragment of 1.7 kb containing a part of the ilvE gene and a part of the 5'-terminal side of the ilvD gene. The both were ligated with each other to obtain a DNA mixture which was used to transform a dihydroxyacid dehydratase (ilvD gene product)-deficient strain, i.e., AB1280 strain. A transformant strain, from which the branched chain amino acid auxotrophy disappeared, was selected from transformed strains. When a plasmid was prepared from the obtained transformant strain, a DNA fragment obtained by digesting pMWGMA2 only at the HindIII site existing between AattGM and ilvA was ligated with the HindIII-HindIII DNA fragment of 1.7 kb originating from pUCE1 and containing a part of the ilvE gene and a part of the ilvD gene, in which ilvGMEDA operon was regenerated. The plasmid thus obtained was designated as pMWD5. The procedure for constructing pMWD5 as described above is summarized in FIG. 4.

The plasmid pMWD5 (Ap$^r$) obtained as described above is a plasmid based on the use of pMW119 as a vector, which carries ilvGMEDA operon from which the region necessary for attenuation is removed.

(3) Creation of L-Isoleucine-Producing Bacterium pVIC40-pps was introduced into *Escherichia coli* VNII-Genetika TDH-6 (TDH-6 strain corresponds to a host bacterium obtained by deleting the plasmid pVIC40 from *Escherichia coli* VKPM B-3996 strain described above) to select a transformant by using Sm$^r$ as an index. Further, pMWD5 was introduced thereinto to obtain a transformant TDH-6/pVIC40-pps,pMWD5 exhibiting Sm$^r$ and Ap$^r$. On the other hand, pVIC40 and pMWD5 were introduced into TDH-6 described above by using Sm$^r$ and Ap$^r$ as indexes to obtain TDH-6/pVIC40,pMWD5.

<2>Evaluation of L-Isoleucine Productivity

TDH-6/pVIC40-pps,pMWD5 was cultivated at 37° C. for 24 hours by using an L-isoleucine-producing medium (containing 40 g of glucose, 16 g of ammonium sulfate, 1 g of potassium primary phosphate, 1 g of magnesium sulfate heptahydrate, 0.01 g of ferrous sulfate heptahydrate, 0.01 g of manganese chloride tetrahydrate, 2 g of yeast extract, and 40 g of calcium carbonate in 1 L of water, pH=7.0). TDH-6/pVIC40,pMWD5 was cultivated as a control in the same manner as described above. L-Isoleucine contained in the medium was quantitatively determined by means of high performance liquid chromatography. Results are shown in Table 4.

TABLE 4

| Bacterial strain | Amount of produced L-isoleucine (g/L) |
| --- | --- |
| TDH-6/pVIC40,pMWD5 | 10.0 |
| TDH-6/pVIC40-pps,pMWD5 | 11.5 |

Industrial Applicability

According to the present invention, it is possible to produce, at a high yield, various amino acids represented by aromatic amino acids, especially L-phenylalanine, L-tryptophane, L-tyrosine, L-threonine, and L-isoleucine. The productivity of these L-amino acids can be further enhanced by applying the present invention to the microorganism having the high productivity of these L-amino acids.

What is claimed is:

1. A method for producing L-amino acid comprising cultivating in a medium a recombinant microorganism having an enhanced L-amino acid-producing ability, producing and accumulating the L-amino acid in the medium, and collecting the L-amino acid, wherein said amino acid is L-threonine or L-isoleucine, and wherein the said recombinant microorganism transformed with a gene encoding phosphoenolpyruvate synthase and a threonine operon comprising a gene coding for aspartokinase desensitized for feedback inhibition by L-threonine.

2. The method according to claim 1, wherein the L-amino acid is L-threonine.

3. The method according to claim 1, wherein the L-amino acid is L-isoleucine and wherein the said recombinant microorganism containing an ilvGMEDA operon comprising a gene coding for threonine deaminase desensitized for feedback inhibition by L-isoleucine.

4. The method according to claim 1, wherein the microorganism is a Escherichia bacterium.

5. The method according to claim 1, wherein the microorganism is a coryneform bacterium.

6. The method according to claim 1 wherein the recombinant microorganism comprises multicopies of the said gene coding for phosphoenolpyruvate synthase.

* * * * *

SEQUENCE LISTING

<160> NUMBER OF SEQ ID NOS: 11

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
cccgtcgacg gatccagttt catctcttg                                      29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
cccgtcgacg atcatgcgct tatgtcgtg                                      29

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
agaggatcca gagatttctg aagc                                           24

<210> SEQ ID NO 4
<211> LENGTH: 26
<212> TYPE: DNA

```
<213> ORGANISM: Artificial Sequence
<220> FEATURE:
<223> OTHER INFORMATION: Description of Artificial Sequence:Synthetic
      DNA

<400> SEQUENCE: 4
tctggatccg caaacggaca ttatca                                          26

<210> SEQ ID NO 5
<211> LENGTH: 2841
<212> TYPE: DNA
<213> ORGANISM: Escherichia coli
<220> FEATURE:
<221> NAME/KEY: CDS
<222> LOCATION: (957)..(1055)
<220> FEATURE:
<221> NAME/KEY: CDS
<222> LOCATION: (1081)..(1104)
<220> FEATURE:
<221> NAME/KEY: CDS
<222> LOCATION: (1195)..(2841)
<220> FEATURE:
<221> NAME/KEY: misc_feature
<222> LOCATION: (52)..(57)
<223> OTHER INFORMATION: cleavage site (SmaI)
<220> FEATURE:
<221> NAME/KEY: misc_feature
<222> LOCATION: (2395)..(2400)
<223> OTHER INFORMATION: cleavage site (KpnI)

<400> SEQUENCE: 5
```

| | |
|---|---:|
| ctcgctttcc ttgttcctga ccgataacat cactgagatc atgttgtagc gcccgggata | 60 |
| ctgcatcagt tggtttcggg cgttcgagag cgtgcttacc ttccagaaac gcacagacag | 120 |
| cttgcagatg atcggctatc aggcatcctt caccgttaat tagccccact tcatcttcgt | 180 |
| tatctttcgc gacgataatt tttctgcccg acttaatagc ttcagttgca ctggagattg | 240 |
| cgccgggaac gccacgcaga gcgcctgtaa gcgccagttc tccgactaat tcatattcat | 300 |
| ctaacttatt ggctgtaagc tgttctgagg ccgccagcaa cgcaatggcg ataggtaaat | 360 |
| catatcgtcc cccttctttt ggcagatcag ctggagccag ttgatggtg atttttttcg | 420 |
| ccggatattc atatccgcta ttgataatgg cgctgcgcac gcgatcgcga cttctttta | 480 |
| ccgttgtttc tggtaagccc accatcgtta agccgggtag acctttactg atatgtacct | 540 |
| caacagtgat cgggggcgca tttactccca gggctgcgcg ggtatgaaca attgacagtg | 600 |
| acataagccc tccttgagtc accattatgt gcataagata tcgctgctgt agcccgctaa | 660 |
| ttcgtgaatt ttagtggctg attcctgttt atttgtgcaa gtgaagttga gttgttctgg | 720 |
| cggtggaatg atgctcgcaa aaatgcagcg gacaaaggat gaactacgag gaagggaaca | 780 |
| acattcatac tgaaattgaa ttttttttcac tcactatttt atttttaaaa aacaacaatt | 840 |
| tatattgaaa ttattaaacg catcataaaa atcggccaaa aaatatcttg tactatttac | 900 |
| aaaacctatg gtaactcttt aggcattcct tcgaacaaga tgcaagaaaa gacaaa atg | 959 |
|                                                                                                     Met<br>                                                                                                       1 | |
| aca gcc ctt cta cga gtg att agc ctg gtc gtg att agc gtg gtg gtg<br>Thr Ala Leu Leu Arg Val Ile Ser Leu Val Val Ile Ser Val Val Val<br>                 5                     10                     15 | 1007 |
| att atc atc cca ccg tgc ggg gct gca ctt gga cga gga aag gct tag<br>Ile Ile Ile Pro Pro Cys Gly Ala Ala Leu Gly Arg Gly Lys Ala<br>              20                     25                     30 | 1055 |
| agatcaagcc ttaacgaact aagac ccc cgc acc gaa agg tcc ggg ggt<br>                                           Pro Arg Thr Glu Arg Ser Gly Gly<br>                                            35                     40 | 1104 |

-continued

```
tttttttgac cttaaaaaca taaccgagga gcagacaatg aataacagca caaaattctg      1164
tttctcaaga ttcaggacgg ggaactaact atg aat ggc gca cag tgg gtg gta      1218
                                 Met Asn Gly Ala Gln Trp Val Val
                                                          45
```

| | | | | | | | | | | | | | | | | |
|---|---|---|---|---|---|---|---|---|---|---|---|---|---|---|---|---|
| cat | gcg | ttg | cgg | gca | cag | ggt | gtg | aac | acc | gtt | ttc | ggt | tat | ccg | ggt | 1266 |
| His | Ala | Leu | Arg | Ala | Gln | Gly | Val | Asn | Thr | Val | Phe | Gly | Tyr | Pro | Gly | |
| 50 | | | | 55 | | | | | 60 | | | | | 65 | | |
| ggc | gca | att | atg | ccg | gtt | tac | gat | gca | ttg | tat | gac | ggc | ggc | gtg | gag | 1314 |
| Gly | Ala | Ile | Met | Pro | Val | Tyr | Asp | Ala | Leu | Tyr | Asp | Gly | Gly | Val | Glu | |
| | | | 70 | | | | | 75 | | | | | 80 | | | |
| cac | ttg | cta | tgc | cga | cat | gag | cag | ggt | gcg | gca | atg | gcg | gct | atc | ggt | 1362 |
| His | Leu | Leu | Cys | Arg | His | Glu | Gln | Gly | Ala | Ala | Met | Ala | Ala | Ile | Gly | |
| | | | 85 | | | | | 90 | | | | | 95 | | | |
| tat | gct | cgt | gct | acc | ggc | aaa | act | ggc | gta | tgt | atc | gcc | acg | tct | ggt | 1410 |
| Tyr | Ala | Arg | Ala | Thr | Gly | Lys | Thr | Gly | Val | Cys | Ile | Ala | Thr | Ser | Gly | |
| | | | 100 | | | | | 105 | | | | | 110 | | | |
| ccg | ggc | gca | acc | aac | ctg | ata | acc | ggg | ctt | gcg | gac | gca | ctg | tta | gat | 1458 |
| Pro | Gly | Ala | Thr | Asn | Leu | Ile | Thr | Gly | Leu | Ala | Asp | Ala | Leu | Leu | Asp | |
| | | | 115 | | | | | 120 | | | | | 125 | | | |
| tcc | atc | cct | gtt | gtt | gcc | atc | acc | ggt | caa | gtg | tcc | gca | ccg | ttt | atc | 1506 |
| Ser | Ile | Pro | Val | Val | Ala | Ile | Thr | Gly | Gln | Val | Ser | Ala | Pro | Phe | Ile | |
| 130 | | | | 135 | | | | | 140 | | | | | 145 | | |
| ggc | act | gac | gca | ttt | cag | gaa | gtg | gat | gtc | ctg | gga | ttg | tcg | tta | gcc | 1554 |
| Gly | Thr | Asp | Ala | Phe | Gln | Glu | Val | Asp | Val | Leu | Gly | Leu | Ser | Leu | Ala | |
| | | | 150 | | | | | 155 | | | | | 160 | | | |
| tgt | acc | aag | cat | agc | ttt | ctg | gtg | cag | tcg | ctg | gaa | gag | ttg | ccg | cgc | 1602 |
| Cys | Thr | Lys | His | Ser | Phe | Leu | Val | Gln | Ser | Leu | Glu | Glu | Leu | Pro | Arg | |
| | | | 165 | | | | | 170 | | | | | 175 | | | |
| atc | atg | gct | gaa | gca | ttc | gac | gtt | gcc | tgc | tca | ggt | cgt | cct | ggt | ccg | 1650 |
| Ile | Met | Ala | Glu | Ala | Phe | Asp | Val | Ala | Cys | Ser | Gly | Arg | Pro | Gly | Pro | |
| | | | 180 | | | | | 185 | | | | | 190 | | | |
| gtt | ctg | gtc | gat | atc | cca | aaa | gat | atc | cag | tta | gcc | agc | ggt | gac | ctg | 1698 |
| Val | Leu | Val | Asp | Ile | Pro | Lys | Asp | Ile | Gln | Leu | Ala | Ser | Gly | Asp | Leu | |
| | | | 195 | | | | | 200 | | | | | 205 | | | |
| gaa | ccg | tgg | ttc | acc | acc | gtt | gaa | aac | gaa | gtg | act | ttc | cca | cat | gcc | 1746 |
| Glu | Pro | Trp | Phe | Thr | Thr | Val | Glu | Asn | Glu | Val | Thr | Phe | Pro | His | Ala | |
| 210 | | | | 215 | | | | | 220 | | | | | 225 | | |
| gaa | gtt | gag | caa | gcg | cgc | cag | atg | ctg | gca | aaa | gcg | caa | aaa | ccg | atg | 1794 |
| Glu | Val | Glu | Gln | Ala | Arg | Gln | Met | Leu | Ala | Lys | Ala | Gln | Lys | Pro | Met | |
| | | | 230 | | | | | 235 | | | | | 240 | | | |
| ctg | tac | gtt | ggc | ggt | ggc | gtg | ggt | atg | gcg | cag | gca | gtt | ccg | gct | ttg | 1842 |
| Leu | Tyr | Val | Gly | Gly | Gly | Val | Gly | Met | Ala | Gln | Ala | Val | Pro | Ala | Leu | |
| | | | 245 | | | | | 250 | | | | | 255 | | | |
| cgt | gaa | ttt | ctc | gct | gcc | aca | aaa | atg | cct | gcc | acc | tgt | acg | ctg | aaa | 1890 |
| Arg | Glu | Phe | Leu | Ala | Ala | Thr | Lys | Met | Pro | Ala | Thr | Cys | Thr | Leu | Lys | |
| | | | 260 | | | | | 265 | | | | | 270 | | | |
| ggg | ctg | ggc | gca | gta | gaa | gca | gat | tat | ccg | tac | tat | ctg | ggc | atg | ctg | 1938 |
| Gly | Leu | Gly | Ala | Val | Glu | Ala | Asp | Tyr | Pro | Tyr | Tyr | Leu | Gly | Met | Leu | |
| | | | 275 | | | | | 280 | | | | | 285 | | | |
| ggg | atg | cac | ggc | acc | aaa | gcg | gca | aac | ttc | gcg | gtg | cag | gag | tgt | gac | 1986 |
| Gly | Met | His | Gly | Thr | Lys | Ala | Ala | Asn | Phe | Ala | Val | Gln | Glu | Cys | Asp | |
| 290 | | | | 295 | | | | | 300 | | | | | 305 | | |
| ctg | ctg | atc | gcc | gtg | ggc | gca | cgt | ttt | gat | gac | cgg | gtg | acc | ggc | aaa | 2034 |
| Leu | Leu | Ile | Ala | Val | Gly | Ala | Arg | Phe | Asp | Asp | Arg | Val | Thr | Gly | Lys | |
| | | | 310 | | | | | 315 | | | | | 320 | | | |
| ctg | aac | acc | ttc | gcg | cca | cac | gcc | agt | gtt | atc | cat | atg | gat | atc | gac | 2082 |
| Leu | Asn | Thr | Phe | Ala | Pro | His | Ala | Ser | Val | Ile | His | Met | Asp | Ile | Asp | |
| | | | 325 | | | | | 330 | | | | | 335 | | | |

| | |
|---|---|
| ccg gca gaa atg aac aag ctg cgt cag gca cat gtg gca tta caa ggt<br>Pro Ala Glu Met Asn Lys Leu Arg Gln Ala His Val Ala Leu Gln Gly<br>        340                        345                    350 | 2130 |
| gat tta aat gct ctg tta cca gca tta cag cag ccg tta aat caa tgt<br>Asp Leu Asn Ala Leu Leu Pro Ala Leu Gln Gln Pro Leu Asn Gln Cys<br>355                        360                        365 | 2178 |
| gac tgg cag caa cac tgc gcg cag ctg cgt gat gaa cat tcc tgg cgt<br>Asp Trp Gln Gln His Cys Ala Gln Leu Arg Asp Glu His Ser Trp Arg<br>370                        375                        380                        385 | 2226 |
| tac gac cat ccc ggt gac gct atc tac gcg ccg ttg tta aaa caa<br>Tyr Asp His Pro Gly Asp Ala Ile Tyr Ala Pro Leu Leu Leu Lys Gln<br>                    390                        395                    400 | 2274 |
| ctg tcg gat cgt aaa cct gcg gat tgc gtc gtg acc aca gat gtg ggg<br>Leu Ser Asp Arg Lys Pro Ala Asp Cys Val Val Thr Thr Asp Val Gly<br>                  405                        410                    415 | 2322 |
| cag cac cag atg tgg gct gcg cag cac atc gcc cac act cgc ccg gaa<br>Gln His Gln Met Trp Ala Ala Gln His Ile Ala His Thr Arg Pro Glu<br>                    420                        425                    430 | 2370 |
| aat ttc atc acc tcc agc ggt tta ggt acc atg ggt ttt ggt tta ccg<br>Asn Phe Ile Thr Ser Ser Gly Leu Gly Thr Met Gly Phe Gly Leu Pro<br>435                        440                        445 | 2418 |
| gcg gcg gtt ggc gca caa gtc gcg cga ccg aac gat acc gtt gtc tgt<br>Ala Ala Val Gly Ala Gln Val Ala Arg Pro Asn Asp Thr Val Val Cys<br>450                        455                        460                    465 | 2466 |
| atc tcc ggt gac ggc tct ttc atg atg aat gtg caa gag ctg ggc acc<br>Ile Ser Gly Asp Gly Ser Phe Met Met Asn Val Gln Glu Leu Gly Thr<br>                    470                        475                    480 | 2514 |
| gta aaa cgc aag cag tta ccg ttg aaa atc gtc tta ctc gat aac caa<br>Val Lys Arg Lys Gln Leu Pro Leu Lys Ile Val Leu Leu Asp Asn Gln<br>                    485                        490                    495 | 2562 |
| cgg tta ggg atg gtt cga caa tgg cag caa ctg ttt ttt cag gaa cga<br>Arg Leu Gly Met Val Arg Gln Trp Gln Gln Leu Phe Phe Gln Glu Arg<br>                500                        505                    510 | 2610 |
| tac agc gaa acc acc ctt act gat aac ccc gat ttc ctc atg tta gcc<br>Tyr Ser Glu Thr Thr Leu Thr Asp Asn Pro Asp Phe Leu Met Leu Ala<br>515                        520                        525 | 2658 |
| agc gcc ttc ggc atc cat ggc caa cac atc acc cgg aaa gac cag gtt<br>Ser Ala Phe Gly Ile His Gly Gln His Ile Thr Arg Lys Asp Gln Val<br>530                        535                        540                    545 | 2706 |
| gaa gcg gca ctc gac acc atg ctg aac agt gat ggg cca tac ctg ctt<br>Glu Ala Ala Leu Asp Thr Met Leu Asn Ser Asp Gly Pro Tyr Leu Leu<br>                    550                        555                    560 | 2754 |
| cat gtc tca atc gac gaa ctt gag aac gtc tgg ccg ctg gtg ccg cct<br>His Val Ser Ile Asp Glu Leu Glu Asn Val Trp Pro Leu Val Pro Pro<br>                  565                        570                    575 | 2802 |
| ggc gcc agt aat tca gaa atg ttg gag aaa tta tca tga<br>Gly Ala Ser Asn Ser Glu Met Leu Glu Lys Leu Ser<br>            580                        585                    590 | 2841 |

<210> SEQ ID NO 6
<211> LENGTH: 32
<212> TYPE: PRT
<213> ORGANISM: Escherichia coli

<400> SEQUENCE: 6

Met Thr Ala Leu Leu Arg Val Ile Ser Leu Val Val Ile Ser Val Val
 1              5                   10                 15

Val Ile Ile Ile Pro Pro Cys Gly Ala Ala Leu Gly Arg Gly Lys Ala
              20                   25                 30

<210> SEQ ID NO 7
<211> LENGTH: 556
<212> TYPE: PRT
<213> ORGANISM: Escherichia coli

<400> SEQUENCE: 7

```
Pro Arg Thr Glu Arg Ser Gly Gly Met Asn Gly Ala Gln Trp Val Val
  1               5                  10                  15

His Ala Leu Arg Ala Gln Gly Val Asn Thr Val Phe Gly Tyr Pro Gly
             20                  25                  30

Gly Ala Ile Met Pro Val Tyr Asp Ala Leu Tyr Asp Gly Gly Val Glu
         35                  40                  45

His Leu Leu Cys Arg His Glu Gln Gly Ala Ala Met Ala Ala Ile Gly
     50                  55                  60

Tyr Ala Arg Ala Thr Gly Lys Thr Gly Val Cys Ile Ala Thr Ser Gly
 65                  70                  75                  80

Pro Gly Ala Thr Asn Leu Ile Thr Gly Leu Ala Asp Ala Leu Leu Asp
                 85                  90                  95

Ser Ile Pro Val Val Ala Ile Thr Gly Gln Val Ser Ala Pro Phe Ile
            100                 105                 110

Gly Thr Asp Ala Phe Gln Glu Val Asp Val Leu Gly Leu Ser Leu Ala
        115                 120                 125

Cys Thr Lys His Ser Phe Leu Val Gln Ser Leu Glu Glu Leu Pro Arg
    130                 135                 140

Ile Met Ala Glu Ala Phe Asp Val Ala Cys Ser Gly Arg Pro Gly Pro
145                 150                 155                 160

Val Leu Val Asp Ile Pro Lys Asp Ile Gln Leu Ala Ser Gly Asp Leu
                165                 170                 175

Glu Pro Trp Phe Thr Thr Val Glu Asn Glu Val Thr Phe Pro His Ala
            180                 185                 190

Glu Val Glu Gln Ala Arg Gln Met Leu Ala Lys Ala Gln Lys Pro Met
        195                 200                 205

Leu Tyr Val Gly Gly Gly Val Gly Met Ala Gln Ala Val Pro Ala Leu
    210                 215                 220

Arg Glu Phe Leu Ala Ala Thr Lys Met Pro Ala Thr Cys Thr Leu Lys
225                 230                 235                 240

Gly Leu Gly Ala Val Glu Ala Asp Tyr Pro Tyr Tyr Leu Gly Met Leu
                245                 250                 255

Gly Met His Gly Thr Lys Ala Ala Asn Phe Ala Val Gln Glu Cys Asp
            260                 265                 270

Leu Leu Ile Ala Val Gly Ala Arg Phe Asp Asp Arg Val Thr Gly Lys
        275                 280                 285

Leu Asn Thr Phe Ala Pro His Ala Ser Val Ile His Met Asp Ile Asp
    290                 295                 300

Pro Ala Glu Met Asn Lys Leu Arg Gln Ala His Val Ala Leu Gln Gly
305                 310                 315                 320

Asp Leu Asn Ala Leu Leu Pro Ala Leu Gln Gln Pro Leu Asn Gln Cys
                325                 330                 335

Asp Trp Gln Gln His Cys Ala Gln Leu Arg Asp Glu His Ser Trp Arg
            340                 345                 350

Tyr Asp His Pro Gly Asp Ala Ile Tyr Ala Pro Leu Leu Leu Lys Gln
        355                 360                 365

Leu Ser Asp Arg Lys Pro Ala Asp Cys Val Val Thr Thr Asp Val Gly
    370                 375                 380
```

Gln His Gln Met Trp Ala Ala Gln His Ile Ala His Thr Arg Pro Glu
385                 390                 395                 400

Asn Phe Ile Thr Ser Ser Gly Leu Gly Thr Met Gly Phe Gly Leu Pro
            405                 410                 415

Ala Ala Val Gly Ala Gln Val Ala Arg Pro Asn Asp Thr Val Val Cys
                420                 425                 430

Ile Ser Gly Asp Gly Ser Phe Met Met Asn Val Gln Glu Leu Gly Thr
            435                 440                 445

Val Lys Arg Lys Gln Leu Pro Leu Lys Ile Val Leu Leu Asp Asn Gln
        450                 455                 460

Arg Leu Gly Met Val Arg Gln Trp Gln Gln Leu Phe Phe Gln Glu Arg
465                 470                 475                 480

Tyr Ser Glu Thr Thr Leu Thr Asp Asn Pro Asp Phe Leu Met Leu Ala
                485                 490                 495

Ser Ala Phe Gly Ile His Gly Gln His Ile Thr Arg Lys Asp Gln Val
            500                 505                 510

Glu Ala Ala Leu Asp Thr Met Leu Asn Ser Asp Gly Pro Tyr Leu Leu
            515                 520                 525

His Val Ser Ile Asp Glu Leu Glu Asn Val Trp Pro Leu Val Pro Pro
        530                 535                 540

Gly Ala Ser Asn Ser Glu Met Leu Glu Lys Leu Ser
545                 550                 555

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
taacatcact gagatcatgt tg                                          22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
tcttttcttg catcttgttc g                                           21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
tctgtttctc aagattcagg ac                                          22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:Synthetic -continued

```
            DNA

<400> SEQUENCE: 11
cgccggtaaa ccaaaaccc                                                      19
```